United States Patent [19]

Aurell et al.

[11] 4,028,318

[45] June 7, 1977

[54] CHROMOGENIC ENZYME SUBSTRATES

[75] Inventors: Leif Erik Aurell, Molndal; Karl Göran Claeson, Saro, both of Sweden

[73] Assignee: A B Kabi, Stockholm, Sweden

[22] Filed: Nov. 14, 1975

[21] Appl. No.: 631,974

[30] Foreign Application Priority Data

Dec. 5, 1974 Sweden .................... 7415229

[52] U.S. Cl. ............... 260/112.5 R; 195/103.5 R
[51] Int. Cl.² ......................... C07C 103/52
[58] Field of Search .................. 260/112.5 R

[56] References Cited

UNITED STATES PATENTS

| | | | |
|---|---|---|---|
| 3,778,426 | 12/1973 | Najjar .................... | 260/112.5 R |
| 3,884,896 | 5/1975 | Blomback et al. .......... | 260/112.5 R |
| 3,896,103 | 5/1975 | Hardy et al. ............. | 260/112.5 R |

*Primary Examiner*—Delbert R. Philips
*Attorney, Agent, or Firm*—Pollock, Vande Sande & Priddy

[57] ABSTRACT

Chromogenic substrates for serine proteases, represented by the formula:

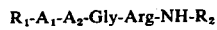

$R_1$-$A_1$-$A_2$-Gly-Arg-NH-$R_2$ or its salts, where $R_1$ is hydrogen or alkanoyl having from 1 to 12 carbon atoms or cyclohexylcarbonyl or benzoyl or benzoyl substituted with one or two halogen atoms, methylamine or phenyl groups or benzene sulphonyl or toluenesulphonyl, $R_2$ is nitrophenyl or naphthyl or nitronaphthyl or methoxynaphthyl or quinolyl or nitroquinolyl, $A_1$ is a single bond or one of the amino acids Gly, Ala, Val, Leu, Ileu, Pro, Met, Phe or Tyr, and $A_2$ is one of the amino acids Glu, Gln, Asp, or Asn.

9 Claims, No Drawings

CHROMOGENIC ENZYME SUBSTRATES

The present invention deals with new chromogenic substrates for serine proteases. These new substrates are especially suitable for determination of factor Xa (E.C. 3. 4. 21. 6) or for the study of reactions causing Xa to be formed, inhibited or consumed, or even for the determination of such factors that influence, or participate in such reactions.

Factor X is a key substance in the series of reactions leading to the coagulation of blood. The activation of factor X brings about the formation of the proteolytic enzyme, factor Xa, which is directly responsible for the transference of prothrombin to thrombin. The availability of a simple method for determining factor Xa would be very valuable for diagnosis.

The hitherto used reagents for factor Xa determination, have usually consisted of ester substrates of very unspecific character. One of these is, e.g. p-nitrophenyl-p-guanidinobenzoate (p-NPGB), which is a good substrate for thrombin, trypsin and plasmin as well. Its practicability for factor Xa is limited to being used for purified enzyme preparations. The results obtained when using blood are not practicable because of the presence of other esterases with activity for p-NPGB (R. L. Smith, J. Biol. Chem. 248, 2418 (1972).

Very good chromogenic amide substrates for enzymes resembling thrombin, have been described in the Swedish Patent Application No. 5757/72. One of these, with the formula Benzoyl-Phe-Val-Arg-p-nitroanilide(S-2160) works very well for thrombin, whereas, when used with factor Xa, it is split only slightly. The susceptibility of a substrate towards thrombin, should be negligible if it is to be used for factor Xa in diagnostic blood analyses.

The availability of a substrate more specific to factor Xa, and therefore less susceptible to splitting by thrombin, would thus be desirable. The substrate should measure the biological function of the enzyme, that is to split amide bonds. Furthermore it is desirable that the substrate can be split rapidly into easily measured products such as chromophoric compounds that readily can be followed spectrophotometrically.

The new substrates according to the invention are of the amide type, they have a high sensitivity to factor Xa and they are represented by the following general formula:

$$B_1 - A_1 - A_2 - Gly - Arg - NH - R_2$$

or its salts, where $R_1$ may be selected from hydrogen, an alkanoyl having from 1 to 12 carbon atoms, cyclohexylcarbonyl, benzoyl, a benzoyl substituted with e.g. one or two halogen atoms, methyl-, amino- or phenyl groups, benzenesulphonyl and 4-toluene-sulphonyl. $R_2$ may be selected from nitrophenyl, naphthyl, nitronaphthyl, methoxynaphthyl, quinolyl and nitroquinolyl. $A_1$ may be a single bond, or it can be selected from the amino acids Gly, Ala, Val, Leu, Ileu, Pro, Met, Phe and Tyr. $A_2$ maybe selected from the amino acids Glu, Gln, Asp and Asn. Some examples of substrates of the present invention are benzoyl-Ileu-Glu-Gly-Arg-p-nitroanilide, H-Phe-Glu-Gly-Arg-p-nitroanilide, benzoyl-Leu-Glu-Gly-Arg-p-nitroanilide, benzoyl-Val-Glu-Gly-Arg-p-nitroanilide, benzoyl-Leu-Asp-Gly-Arg-p-nitroanilide, benzoyl-Ileu-Glu-Gly-Arg-2-naphthylamide, benzoyl-Ileu-Glu-Gly-Arg-4-methoxy-2-naphthylamide, and benzoyl-Ileu-Gln-Gly-Arg-p-nitroanilide.

The new substrates may be produced according to two principally different methods.

1. The first method is based upon the coupling of the chromophoric group $R_2$ to the arginine and then a step-by-step building up of the desired peptide structure by means of gradual coupling of the remaining amino acids. The chromophoric group is here used as a blocking group for the C-terminal carboxyl group of the first amino acids.

2. The other method is based upon a step-by-step building up of the desired peptide structure, after which the used blocking groups are removed and the chromophoric group $R_2$ is coupled to the peptide structure.

In using this step-by-step synthesis of the peptide structure according to these two methods, it is possible to adequately purify by means of gelfiltration following each coupling of a new amino acid.

The coupling methods that have been used in this stepwise synthesis of the peptide derivatives are well known and commonly used in peptide chemistry. Well known and within peptide chemistry commonly used blocking groups, such as Cbo (carbobenzoxy), MeOCbo (p-methoxycarbobenzoxy), $NO_2Cbo$ (p-nitrocarbobenzoxy), MCbo (p-methoxyphenylazo-carbobenzoxy), BOC (tert.-butyloxycarbonyl), TFA (trifluoroacetyl) or formyl are used as amino blocking groups. The α-carboxyl group can be activated by means of conversion to different activated, in peptide chemistry well-known and often used derivatives, which may either be isolated or generated in situ, as for example p-nitrophenylester, trichlorophenylester, pentachlorophenylester, N-hydroxysuccinimide ester, acid azide, acid anhydride, which may either be symmetric or unsymmetric. It may also be activated with a carbodiimide such as N,N-dicyclohexycarbodiimide. The C-terminal carboxyl group in the amino peptide derivative or the amino acid derivative may be protected by esterifying to e.g. methyl-, ethyl- or isopropylester or by means of conversion to the chromophoric aniline derivative, which thus works as a blocking group during the building up of the peptide chain. Those free functional groups which do not take part in the reaction, may during the synthesis of the peptides or the peptide derivatives be protected in the following manner:

For the purpose of blocking the remaining arginyl δ-guanido group one may use such amino blocking groups, commonly used within peptide chemistry, as for example protonization, $NO_2$ or Tos (p-toluenesulphonyl). As protection for the carboxyl group in glutamic and aspartic acid, one may use such blocking groups that are commonly used in peptide chemistry, such as the benzyl and tertiary butyl protection groups.

The invention will be described in greater detail in the following examples demonstrating the production of different substrates according to the invention by means of the stepwise synthesis.

In the thin layer chromatographic analysis of eluates and products, glassplates with silica gel $F_{254}$ (Merck) were used as absorption medium. The solvent systems used have been designated according to the following table:

| Designation | Solvents | Relations to volume |
| --- | --- | --- |
| A | n-butanol:acetic acid:water | (3:1:1) |
| C | n-propanol:ethyl acetate:water | (7:1:2) |

-continued

| Designation | Solvents | Relations to volume |
|---|---|---|
| D | n-heptane:n-butanol:acetic acid | (3:2:1) |
| P$_1$ | chloroform:methanol | (9:1) |

After the thin layer chromatographing, the plates were studied first in UV-light (254 nm) and subsequently by using the chlorine/toluidinereaction (Ref.: G. Pataki: Dunnschicht- chromatografie in der Aminosaure- und Peptidchemie, Walter de Gruyter & Co. Berlin, 1966, p. 125) as a development method.

The meanings of the abbreviations used below are the following: Amino acids:

These abbreviations refer to aminoacid rests. The free aminoacid of peptide is indicated by means of H— at the amino group and —OH at the carboxyl group. The amino group is always indicated to the left, the carboxyl group to the right.

Unless otherwise stated, all amino acids used have the L-configuration.

Ala = Alanine
Arg = Arginine
Asn = Asparagine
Asp = Aspartic acid
Gln = Glutamine
Glu = Glutamic acid
Gly = Glycine
Ileu = Isoleucine
Leu = Leucine
Met = Methionine
Phe = Phenylalanine
Pro = Proline
Tyr = Tyrosine
Val = Valine Further abbreviations:
Ac = Acetyl
Ac$_2$O = Acetic anhydride
AcOH = Acetic acid
BOC = Tert.-Butyloxycarbonyl
Bz = Benzoyl
Bzl = Benzyl
Bz$_2$O = Benzoic anhydride
Cbo = Carbobenzoxy
DCCI = Dicyclohexylcarbodiimide
DMF = Dimethylformamide
Et$_3$N = Triethylamine
MCba = p-Methoxyphenylazocarbobenzoxy
MeOH = Methanol
OtBU = Tert.-Butyloxy
OEt = Ethyloxy
OMe = Methyloxy
OpNP = p-Nitrophenoxy
OisoPr = iso-Propyloxy
pNA = p-Nitroanilide
TFA = Trifluoroacetyl
Tos = p-Toluenesulphonyl Unless otherwise stated, the temperature indications in the examples are ° C.

Example I:HCl.Bz-Ileu-Glu-Gly-Arg-pNA Ia:
Cbo-Gly-Arg-(NO$_2$)-pNA (M.w. 530.4

5.0 g (10.6 mmoles) of Cbo-Arg(NO$_2$is dissolved in 21 ml of AcOH and 22 ml of 4N HBr in AcOH under moisture-free conditions. The solution is stirred for one hour at room temperature and thereafter it is slowly poured into 200 ml of vigorously stirred ether. The ether solution is decanted, and the obtained grannular residue is treated another two times with 100 ml of ether. After drying in vacuo over P$_2$O$_5$ and pellets of KOH at 30° C, the yield of the hydrobromide salt of the amino acid derivative is nearly quantitative (4.95 g). The product is homogeneous according to TLC in A.

The product above is dissolved in 50ml of distilled DMF. The solution is cooled to −10° C and Et$_3$N is added until the solution is neutral (2.1 ml). Precipitated Et$_3$N. HBr is filtered and the filtrate is cooled to −10° C. 3.9 g (11.8 mmole) of Cbo-Gyl-OpNP is added and the solution may slowly arise to room temperature. After three hours the solution is again cooled to −10° C and buffered with 0.54 g (5.3 mmole) of Et$_3$N. The buffering procedure is repeated once more after 2–3 hours. The reaction solution is left over night and then evaporated in vacuo at 40° C. The remaining heavy oil is stirred carefuly with 100 ml of distilled water. The water is decanted and the washing procedure is repeated further two times. The remaining oil is dissolved in warm MeOH and on cooling the product precipitates in crystalline form.

Yield: 4.2 g (75% of Ia; Homogeneous according to TLC in P$_1$ (R$_f$= 0.16); [α]$_D^{24}$ −36° (c 0.50, MeOH).

Ib: t-Boc-Glu-(γ-OBzl)-Gly-Arg(NO$_2$)-pNA (M.w. 715.8)

2.65 g (5.0 mmole) of Ia is decarbobenzoxylated and coupled with 2.50 g (5.5 mmole) of t-Boc-Glu(γ-OBzl)-OpNP according to the method in example Ia. The crude product is purified by gel chromatography on a column containing SEPHADEX LH-20 in MeOH.

Yield: 3.25 g (91%) of Ib; Homogeneous according to TLC in P$_1$ (R$_f$ = 0.22); [α]$_D^{24}$ −34° (c 1.0, MeOH).

Ic: Cbo-Ileu-Glu(γ-OBzl)-Gly-Arg(NO$_2$)-pNA (M.w. 862.9)

1.08 g (1.5 mmole) of Ib is dissolved in 10 ml of TFA. The solution is stirred for one hour at room temperature, and thereafter it is slowly poured into 75 ml of vigorously stirred, dry ether. The ether solution is decanted, and the obtained granular residue is treated another two times with 50 ml of ether. After drying in vacuo over P$_2$O$_5$ and pellets of KOH at 30° C, the yield of the TFA salt of the tripeptide derivative is nearly quantitative (1.08 g).

The product is homogeneous according to TLC in A. The product above is dissolved in 20 ml of DMF. The solution is cooled to −10° C and neutralized with Et$_3$N (0.23 ml). 0.65 (1.68 mmole) of Cbo-Ileu-O$_p$NP is added and the solution may slowly arise to room temperature. After about 3 hours the solution is again cooled to −10° C and buffered with 0.12 ml of Et$_3$N. The buffering procedure is repeated once more after 2–3 hours and the solution is left over night. The excess of Cbo-Ileu-OpNP is then destroyed by addition of about 100 mg (ca 1.4 mmole) of n-butylamine to the solution. (The excess of active ester is unwanted because it is difficult to separate from the tetrapeptide on gel filtration). After about 30 minutes the solution is evaporated in vacuo at 40° C. The remaining heavy oil is washed with three portions of distilled water. The oil is dissolved in MeOH and purified by gel chromatography on a column with SEPHADEX LH-20 in methanol.

Yield: 1.07 g (83%) of Ic, homogeneous according to TLC in P$_1$ (R$_f$= 0.35) [α]$_D^{24}$ −32° (c 0.3, MeOH: DMF, 95:5)

Id: Bz-Ileu-Glu(γ-OBzl)-Gly-Arg(NO$_2$)-pNA 260 mg (0.30 mmole) of Ic is decarbobenzoxylated according to the method in example Ia. The product shows two spots on TLC in A (R$_f$= 0.45 and 0.60) and IR spectroscopy indicates that the product is a mixture of HBr.H-Ileu-Glu(γ-OH)-Gly(-Arg(NO$_2$)-pNA and HBr.H-Ileu-Glu(γ-OBzl)-Gly-Arg(NO$_2$)-pNA. This mixture is reacted with 800 mg (0.35 mmole) of benzoic anhydride according to the method in example Ia. The crude benzoylated product is purified on a column with SEPHADEX LH-20 in methanol. Two fractions are obtained, α: 130 mg, $[α]_D^{24}$ −15° (c 0.5, $CH_3CN$), Rf = 0.20 in $P_1$ and β: 105 mg, $[α]_D^{24}$ −11° (c 0.5, $CH_3CN$), $R_f$ = 0.06 in $P_1$. IR spectroscopy indicates that the two fractions are Bz-Ileu-Glu(γOBzl)-Gly-Arg($NO_2$)-pNA and Bz-Ileu-Glu-Gly-Arg($NO_2$)-pNA. (Reaction with HF gives from both of the fractions the same final product, Ie).

Ie: HCl.Bz-Ileu-Glu-Gly-Arg-pNA (M.w. 734.3)

100 mg (0.12 mmole) of Id fraction α and 0.5 ml of anisol are placed in the reaction vessel of a Sakakibara apparatus. About 5 ml of dry hydrogen fluoride is distilled into the vessel and allowed to react for 75 min under stirring at 0° C. The hydrogen fluoride is then distilled off under reduced pressure and the oily residue is dissolved in 10 ml of AcOH (33% in water) and purified by chromatography on a column with SEPHADEX G-15 in 33AcOH in water. The fraction of the eluate containing the pure deblocked tetrapeptide derivative is then lyophilized. The obtained compound is dissolved in MeOH:distilled water (95:5) and is chromatographed on a weakly basic anionic exchanger QAE-SEPHADEX A-25 in its chloride form with the same solvent mixture as eluant. The methanol is removed from the eluate at 30° C under reduced pressure and the remaining water solution is lyophilized.

Yield: 75 mg (85%), homogeneous according to TLC in A ($R_f$ = 0.48) $[α]_D^{24}$ −40° (c 0.5, 50% AcOH in dist. water) Amino acid analysis: Ileu: 0.98, Glu: 0.95, Arg: 0.98, Gly: 1.00.

Example II: 2 HCl.H - Ileu-Glu-Gly-Arg-pNA

IIa: 2 HCl.H-Ileu-Gly-Arg-pNA (M.w. 666.6)

100 mg (0.116 mmole) of Ic is reacted with hydrogen fluoride, purified and ionic exchanged according to the methods in example Ie.

Yield: 56 mg (73%), homogeneous according to TLC in A ($R_f$ = 0.34). $[α]_D^{24}$ −35° (c 0.5, 50% AcOH in dist. water)

Amino acid analysis:Ileu: 0.96, Glu: 0.94, Arg: 0.96, Gly: 1.00.

The substrates described in the above examples were used for determination of factor Xa in the following manner: The principle for the determination is based upon the fact that the product formed by the enzymatic hydrolysis presents an UV spectrum that is entirely different from that of the substrate. Thus, the substrate in example I,Bz-Ileu-Glu-Gly-Arg-pNA-HCl, has an absorption maximum at 315 nm with the molar extinction coefficient of 12000. Absorption of the substrate is insignificant at 405 nm. p-Nitroaniline (pNA) which is formed from the substrate during the enzymatic hydrolysis, has an absorption maximum at 380 nm with a molar extinction coefficient of 13200, which decreases only to 9620 at 405 nm. It is therefore possible, by means of measuring spectrophotometrically at 405 nm, to follow with ease the degree of enzymatic hydrolysis which is proportional to the amount of p-nitroaniline produced. The excess of substrate present does not affect the measurement at that wave length. The situation is almost identical for the other substrates in the invention, and for this reason the spectrophotometric measurements were throughout made at 405 nm. Table 1 shows a relative comparison of reaction rates for different enzymes of the type serine proteases (E.C. 3. 4. 21), between the previously mentioned substrate S-2160 and substrate I, according to this invention. The reaction rates are determined according to the method described above.

Table 1

| Conc. | Substrate | Relative reaction rates | | | |
|---|---|---|---|---|---|
| | | Thrombin | Xa | Trypsin | Plasmin |
| 0.1 mM | S-2160 | 100 | 1 | 100 | 100 |
| 0.25 mM | I | 2 | 100 | 500 | 75 |

This table demonstrates that factor Xa splits substrate I 100 times better than is the case with S-2160, and it is affected only to an insignificant extent by thrombin when compared to S-2160. It is thus obvious that I is, according to this comparison, clearly the best substrate for Xa. Furthermore, the table demonstrates that I can successfully be used as a substrate for trypsin as well. However, this positive trypsin effect does not interfer with a determination of factor Xa, since trypsin is not normally present in blood.

The claims defining the invention are as follows:

1. New chromogenic substrates for serine proteases, specially suitable for diagnostic determination of factor Xa, which are represented by the following general formula:

$R_1$-$A_1$-$A_2$-Gly-Arg-NH-$R_2$ or its salts, where $R_1$ is selected from the group consisting of hydrogen, alkanoyl having from 1 to 12 carbon atoms, cyclohexylcarbonyl, benzoyl, benzoyl substituted with one or two halogen atoms, methylamine or phenyl groups, benzene sulphonyl and toluenesulphonyl; $R_2$ is selected from the group consisting of nitrophenyl, naphthyl, nitronaphthyl, methoxynaphthyl, quinolyl and nitroquinolyl; $A_1$ is selected from the group consisting of a single bond, and the amino acids selected from the group consisting of Gly, Ala, Val, Leu, Ileu, Pro, Met, Phe and Tyr; and $A_2$ is selected from the group consisting of the amino acids Glu, Gln, Asp, and Asn.

2. The chromogenic substrate according to claim 1, which is benzoyl-Ileu-Glu-Gly-Arg-p-nitroanilide.

3. The chromogenic substrate according to claim 1, which is H-Phe-Glu-Gly-Arg-p-nitroanilide.

4. The chromogenic substrate according to claim 1, which is benzoyl-Leu-Glu-Gly-Arg-p-nitroamilide.

5. The chromogenic substrate according to claim 1, which is benzoyl-Val-Glu-Gly-Arg-p-nitroanilide.

6. The chromogenic substrate according to claim 1, which is benzoyl-Leu-Asp-Gly-Arg-p-nitroanilide.

7. The chromogenic substrate according to claim 1, which is benzoyl-Ileu-Glu-Gly-Arg-2-naphthylamide.

8. The chromogenic substrate according to claim 1, which is benzoyl-Ileu-Glu-Gly-Arg-4-methoxy-2-naphthylamide.

9. The chromogenic substrate according to claim 1, which is benzoyl-Ileu-Gln-Gly-Arg-p-Nitroanilide.

* * * * *